(12) United States Patent
Ulin et al.

(10) Patent No.: US 8,663,597 B2
(45) Date of Patent: Mar. 4, 2014

(54) METHOD FOR OBTAINING $^{68}$GA

(75) Inventors: Johan Ulin, Uppsala (SE); Bengt Langstrom, Uppsala (SE); Irina Velikyan, Uppsala (SE)

(73) Assignees: GE Healthcare Limited, Buckinghamshire (GB); Hammersmith Imanet Limited, London (GB)

( * ) Notice: Subject to any disclaimer, the term of this patent is extended or adjusted under 35 U.S.C. 154(b) by 0 days.

(21) Appl. No.: 13/395,960

(22) PCT Filed: Sep. 21, 2010
(Under 37 CFR 1.47)

(86) PCT No.: PCT/EP2010/063870
§ 371 (c)(1),
(2), (4) Date: Mar. 14, 2012

(87) PCT Pub. No.: WO2011/033120
PCT Pub. Date: Mar. 24, 2011

(65) Prior Publication Data
US 2012/0178902 A1  Jul. 12, 2012

Related U.S. Application Data

(60) Provisional application No. 61/244,227, filed on Sep. 21, 2009.

(30) Foreign Application Priority Data

Dec. 23, 2009 (GB) .................... 0922492.4

(51) Int. Cl.
*A61K 51/00* (2006.01)
*A61M 36/14* (2006.01)
(52) U.S. Cl.
CPC ...................... *A61K 51/00* (2013.01)
USPC ........................ 424/1.11; 424/1.53
(58) Field of Classification Search
USPC ....................................... 424/1.11
See application file for complete search history.

(56) References Cited

U.S. PATENT DOCUMENTS

2007/0031329 A1 * 2/2007 Velikyan et al. ............. 424/1.49
2009/0001283 A1   1/2009 Fitzsimmons et al.

FOREIGN PATENT DOCUMENTS

| EP | 0054461 | 6/1982 | |
| RU | 2331439 | 8/2008 | |
| WO | 2004/089425 | 10/2004 | |
| WO | 2004/089517 | 10/2004 | |
| WO | 2005/089912 | 9/2005 | |
| WO | WO 2005089912 A1 * | 9/2005 | ............. B01D 59/00 |
| WO | 2006/056395 | 6/2006 | |
| WO | 2008/021302 | 2/2008 | |
| WO | 2009/102378 | 8/2009 | |

OTHER PUBLICATIONS

Meyer et al. (Eu. J. Nucl. Med. Mol. Imaging 2004, 31, 1097-1104).*
Kinoshita et al. (Separation Purification Technol. 2004, 37, 127-133).*
Kopecky, Intl Journal of Applied Radiation and Isotopes, 1973 vol. 24, No. 2, pp. 73-80.
De Blois, Applied Radiation and Isotopes, 2011, vol. 69, No. 2, pp. 308-315.
Wouter, European Journal of Nuclear Medicine and Molecular Imaging, 2005, vol. 32, No. 4.
Lewis, Journal of Labelled Compounds and Radiopharmaceuticals, 1981, vol. 18, No. 1-2, p. 164.
Kulprathipanja, Intl Journal of Applied Radiation and Isotopes, 1977 vol. 28, No. 1-2, pp. 229-233.
GB0922492.4 Search Report Dated Apr. 29, 2010.
PCT/EP2010/063870 Intl Search Report Dated Sep. 20, 2011.

* cited by examiner

*Primary Examiner* — Michael G Hartley
*Assistant Examiner* — Melissa Perreira

(57) ABSTRACT

The present invention relates to a method of obtaining $^{68}$Ga from a $^{68}$Ge/$^{68}$Ga radioisotope generator and a method of preparing $^{68}$Ga-radiolabelled complexes using the obtained $^{68}$Ga. The method comprises elution of the generator with an aqueous chloride ion solution. The invention further relates to an apparatus for carrying out the $^{68}$Ga metal complex formation.

14 Claims, 1 Drawing Sheet

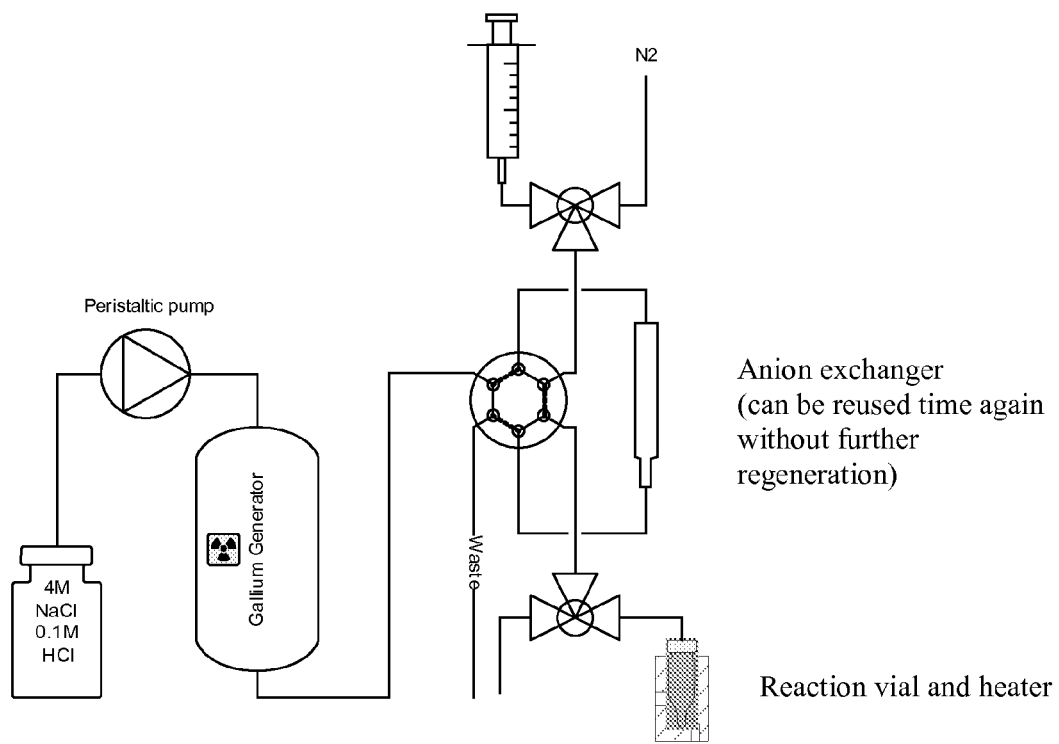
conceptual design of an apparatus of the third aspect.

METHOD FOR OBTAINING $^{68}$GA

This application is a filing under 35 U.S.C. 371 of international application number PCT/EP2010/063870, filed Sep. 21, 2010, which claims priority to Great Britain application number 0922492.4 filed Dec. 23, 2009 and U.S. application No. 61/244,227 filed Sep. 21, 2009, the entire disclosure of which is hereby incorporated by reference.

FIELD OF THE INVENTION

The present invention relates to a method of obtaining $^{68}$Ga from a $^{68}$Ge/$^{68}$Ga radioisotope generator and a method of preparing $^{68}$Ga-radiolabelled complexes using the obtained $^{68}$Ga. The invention further relates to an apparatus for carrying out the $^{68}$Ga metal complex formation.

BACKGROUND TO THE INVENTION $^{68}$Ga is of special interest for the production of Ga-radiolabelled metal complexes used as radiotracer molecules in PET imaging in vivo. $^{68}$Ga is obtained from a $^{68}$Ge/$^{68}$Ga generator, which means that no cyclotron is required. $^{68}$Ga decays 89% by positron emission of 2.92 MeV, and its 68 min half-life is sufficient to follow many biochemical processes in vivo without unnecessary radiation dose to the patient. In the oxidation state of Ga(III), $^{68}$Ga forms stable metal complexes with various types of chelating agents and $^{68}$Ga tracers have been used for brain, renal, bone, blood pool, lung and tumour imaging.

The use of $^{68}$Ga from a $^{68}$Ge/$^{68}$Ga generator for the production of $^{68}$Ga-radiolabelled metal complexes used as PET tracer molecules does, however, have some difficulties. Thus, $^{68}$Ga eluate from a $^{68}$Ge/$^{68}$Ga generator often contains $^{68}$Ge which leads to low radionuclide purity of $^{68}$Ga-radiolabelled metal complexes produced from the $^{68}$Ga eluate. Furthermore, the eluate also contains so-called pseudo carriers, i.e. other metal cations like $Fe^{3+}$, $Al^{3+}$, $Cu^{2+}$, $Zn^{2+}$ and $In^{3+}$, which compete with $^{68}$Ga$^{3+}$ in the subsequent metal complex formation reaction and eventually decrease the specific activity. A further disadvantage is that $^{68}$Ga eluate from a $^{68}$Ge/$^{68}$Ga generator has a low $^{68}$Ga concentration, i.e. in the picomolar to nanomolar range. Consequently, the amount of chelating agent in a subsequent $^{68}$Ga-radiolabelling reaction has to be high for the reaction to take place, which in turn leads to low specific activity. A high amount of chelating agent is especially problematic with $^{68}$Ga-radiolabelled PET radiotracers that comprise a bifunctional chelating agent, i.e. a chelating agent linked to a targeting vector are produced as the patient will receive an unfavourably high amount of these tracers.

J. Schuhmacher et al. [Int. J. Appl. Radiat. Isotopes 32, 31-36 (1981)] describe the use of a Bio-Rad AG 1×8 anion exchanger for treating the 4.5 N HCl $^{68}$Ga eluate obtained from a $^{68}$Ge/$^{68}$Ga generator in order to decrease the amount of $^{68}$Ge present in the eluate. 4 mL water was used to eluate the anion exchanger. A disadvantage of this method is the high volume of water necessary to elute the $^{68}$Ga from the anion exchanger. In order to use this eluate for the production of $^{68}$Ga-radiolabelled PET tracers that comprise a bifunctional chelating agent, the eluate needs to be further concentrated, e.g. by evaporation which in turn leads to a decrease of $^{68}$Ga activity due to the short half-life of this radionuclide.

Velikyan et al [Bioconj. Chem., 15, 554-560 (2004) and WO 2004/089517] disclose an improved method of obtaining $^{68}$Ga, which involves the use of an anion exchange resin comprising $HCO_3^-$ counterions. The Velikyan method for the pre-concentration and purification of the generator eluate is based on anion exchange chromatography and the formation of gallium tetrachloride anion using 4M hydrochloric acid. However, the strong hydrochloric acid used for the acidification is corrosive and hazardous.

The availability of the $^{68}$Ga in pure and concentrated form remains as key requirement for the production of radiotracers with sufficiently high specific radioactivity allowing accurate quantification of PET data.

THE PRESENT INVENTION

The presented invention is aimed at overcoming the complications related to the use of concentrated hydrochloric acid in prior art $^{68}$Ga purification procedures.

The invention provides a method of eluting $^{68}$Ga from a $^{68}$Ge/$^{68}$Ga-generator directly in the form of $^{68}$GaCl$_4^-$ using concentrated chloride ion solutions (preferably NaCl solution of 0.1 M hydrochloric acid), and trapping the formed GaCl$_4^-$ complex directly on an anion exchange resin. This removes the problem of handling 30% HCl, and its corrosive properties handling. It also simplifies the $^{68}$Ga pre-concentration and purification process. Thus, eg. the pH-adjustment later on in the radiolabelling process is simpler, with a possibility to use a lower concentration of buffer. In addition, the anion exchange resin of step (ii) could be reused even without conditioning between preparation runs.

The present method and technology also facilitates GMP (Good Manufacturing Practice) compliance of the method for the pre-concentration and purification of the generator eluate and robustness of the labelling chemistry, so is particularly useful for the preparation of $^{68}$Ga radiopharmaceutical compositions.

DESCRIPTION OF THE FIGURES

FIG. 1 is a conceptual design of an apparatus suitable for carrying out the method of the invention.

DETAILED DESCRIPTION OF THE INVENTION

In a first aspect, the present invention provides a method of obtaining $^{68}$Ga by:
(i) eluting a $^{68}$Ge/$^{68}$Ga radioisotope generator with a chloride ion solution which comprises 0.05-0.2 M aqueous hydrochloric acid solution and has a total chloride ion solution of 3 to 5M concentration, wherein said solution has a pH of less than 2, to give an eluate containing $^{68}$Ga as GaCl$_4^-$;
(ii) passing the eluate from step (i) down an anion exchange resin, wherein the $^{68}$GaCl$_4^-$ is trapped on the resin;
(iii) eluting the trapped $^{68}$GaCl$_4^-$ from step (ii) with water or aqueous buffer solution, to give an aqueous solution of $^{68}$GaCl$_3$.

The term "anion exchange resin" has its conventional meaning.

The abbreviation "M" has its conventional meaning in the context of chemical solutions, and refers to the molarity of the solution.

The chloride ion solution in step (i) suitably has a pH<2. That is because gallium precipitates as gallium hydroxide even at pH 3. That is because the solubility product of gallium hydroxide is very high ($7.28 \times 10^{-36}$). The dilute aqueous hydrochloric acid (HCl) solution has an increased chloride ion concentration by the addition of one or more chloride salts. Such salts are known in the art, and include chloride salts such as NaCl and LiCl. The chloride ion solution of step (i) may optionally comprise further components such as buffers, or chelating agents (eg. EDTA).

Any $^{68}$Ge/$^{68}$Ga radioisotope generator is suitable for use in step (i), although the generator preferably comprises a column comprising titanium dioxide. One such generator is commercially available from Obninsk, Russia. $^{68}$Ga radioisotope generators are described by: Fani et al [Contr. Med. Mol. Imaging, 3(2), 67-77 (2008)]; Maecke et al [Ernst Schering Res. Found. Workshop, (62), 215-242 (2007)]; Loc'h et al, [J. Nucl. Med. 21, 171-173 (1980)] and Schuhmacher et al [Int. J. Appl. Radiat. Isotopes 32, 31-36 (1981)]. $^{68}$Ge may be obtained by cyclotron production by irradiation of, for instance $Ga_2(SO_4)_3$ with 20 MeV protons. It is also commercially available, e.g. as $^{68}$Ge in 0.5 M HCl. Generally, $^{68}$Ge is loaded onto a column consisting of organic resin or an inorganic metal oxide like tin dioxide, aluminium dioxide or titanium dioxide. $^{68}$Ga is eluted from the column with aqueous HCl yielding $^{68}$GaCl$_3$. Thus, $^{68}$Ga is in the form of $^{68}$Ga$^{3+}$, which could be used in the synthesis of $^{68}$Ga-radiolabelled complexes, e.g. for the production of $^{68}$Ga-radiolabelled PET tracers. Suitable columns for $^{68}$Ge/$^{68}$Ga generators consist of inorganic oxides like aluminium dioxide, titanium dioxide or tin dioxide or organic resins like resins comprising phenolic hydroxyl groups (U.S. Pat. No. 4,264,468) or pyrogallol (Schuhmacher et al above). In a preferred embodiment, a $^{68}$Ge/$^{68}$Ga generator having a column comprising. titanium dioxide is used in the method according to the invention.

The water or aqueous buffer solution used in step (iii), breaks down the GaCl$_4^-$ complex, and elutes the $^{68}$Ga quantitatively from the strong anion exchange resin. This has the advantage that small volumes (eg. <600 µl) can be used. Such small elution volumes effectively pre-concentrate the $^{68}$Ga, and provide it in aqueous solution ready for use in the metal complexation reaction of the second aspect (below).

PREFERRED EMBODIMENTS

The chloride ion solution in step (i) preferably comprises 0.06 to 0.14 M HCl, more preferably 0.08 to 0.12 M HCl, most preferably 0.1M HCl. The total chloride ion solution in step (i) preferably has a chloride ion concentration of 3.5 to 4.5 molar, more preferably 3.8 to 4.4 molar, most preferably 4.0 to 4.2 molar. The chloride ion solution is more preferably 4M NaCl and further comprises 0.1 M HCl. The chloride ion concentration is preferably about 4M, since that permits the gallium tetrachloride complex to form, but prevents any contaminating $^{68}$Ge radioisotope from forming the same type of complex.

Before step (iii), it is preferred to wash the trapped $^{68}$GaCl$_4^-$ from step (ii) with more chloride ion solution, in order to remove any excess hydrochloric acid. This stabilises the pH of the reaction mixture and drastically improves the reproducibility of the $^{68}$Ga-radiolabelling procedure of the second aspect.

In step (iii), aqueous buffer is preferably used to elute the $^{68}$Ga from the anion exchange resin.

The anion exchange resin of step (ii) preferably comprises quaternary amine functional groups. The anion exchange resin preferably comprises polystyrene-divinylbenzene.

In a second aspect, the present invention provides a method of producing a $^{68}$Ga-radiolabelled metal complex which comprises:
  (i) obtaining $^{68}$Ga via the method of the first aspect;
  (ii) reacting the $^{68}$Ga from step (i) with a chelating agent, to give the desired $^{68}$Ga metal complex via complexation reaction.

The term "chelating agent" has its conventional meaning. In the second aspect, preferred aspects of the $^{68}$Ga starting material used in step (i) are as described in the first aspect (above).

The term "complexation reaction" has its conventional meaning in the field of coordination chemistry, and refers to the formation of a metal complex with the chelating agent—in this case a metal complex of the radiometal $^{68}$Ga Suitable chelating agents include polyaminopolyacid chelating agents like DTPA, EDTA, DTPA-BMA, DOA3, DOTA, HP-DOA3, TMT or DPDP. Those chelating agents are well known for radiopharmaceuticals and radiotracers. Their use and synthesis are described in, for example, U.S. Pat. Nos. 4,647,447, 5,362,475, 5,534,241, 5,358,704, 5,198,208, 4,963,344; EP 230893 A, EP 130934 A, EP 606683 A, EP 438206 A, EP 434345A, WO 97/00087, WO 96/40274, WO 96/30377, WO 96/28420, WO 96/16678, WO 96/11023, WO 95/32741, WO 95/27705, WO 95/26754, WO 95/28967, WO 95/28392, WO 95/24225, WO 95/17920, WO 95/15319, WO 95/09848, WO 94/27644, WO 94/22368, WO 94/08624, WO 93/16375, WO 93/06868, WO 92/11232, WO 92/09884, WO 92/08707, WO 91/15467, WO 91/10669, WO 91/10645, WO 91/07191, WO 91/05762, WO 90/12050, WO 90/03804, WO 89/00052, WO 89/00557, WO 88/01178, WO 86/02841 and WO 86/02005.

Preferred chelating agents are macrocyclic chelating agents, e.g. porphyrin-like molecules and pentaaza-macrocycles as described by Zhang et al. [Inorg. Chem. 37(5), 956-963 (1998)], phthalocyanines, crown ethers, e.g. nitrogen crown ethers such as the sepulchrates, cryptates etc., hemin (protoporphyrin IX chloride), heme and chelating agents having a square-planar symmetry.

Macrocyclic chelating agents are preferably used in the method of the invention. In a preferred embodiment, these macrocyclic chelating agents comprise at least one hard donor atom such as oxygen and/or nitrogen as in polyaza- and polyoxo-macrocycles. Preferred examples of polyazamacrocyclic chelating agents include DOTA, TRITA, TETA and HETA, with DOTA being particularly preferred.

Particularly preferred macrocyclic chelating agents comprise functional groups such as carboxyl groups or amine groups which are not essential for coordinating to Ga$^{3+}$ and thus may be used to couple other molecules, e.g. targeting vectors, to the chelating agent. Examples of such macrocyclic chelating agents comprising functional groups are DOTA, TRITA or HETA.

The chelating agent is thus preferably a macrocyclic chelating agent, more preferably a bifunctional chelating agent, most preferably a bifunctional chelating agent having conjugated thereto a biological targeting molecule. By the term "biological targeting moiety" (BTM) is meant a compound which, after administration, is taken up selectively or localises at a particular site of the mammalian body in vivo. Such sites may for example be implicated in a particular disease state or be indicative of how an organ or metabolic process is functioning. The BTM may be of synthetic or natural origin, but is preferably synthetic. The term "synthetic" has its conventional meaning, i.e. man-made as opposed to being isolated from natural sources eg. from the mammalian body. Such compounds have the advantage that their manufacture and impurity profile can be fully controlled.

The biological targeting moiety preferably comprises: a 3-100 mer peptide, peptide analogue, peptoid or peptide mimetic which may be a linear or cyclic peptide or combination thereof; a single amino acid; an enzyme substrate, enzyme antagonist enzyme agonist (including partial agonist) or enzyme inhibitor; receptor-binding compound (including a receptor substrate, antagonist, agonist or substrate); oligonucleotides, or oligo-DNA or oligo-RNA fragments.

The complexation reaction of step (ii) is preferably carried out using microwave activation. It has been found that the use of microwave activation substantially improves the efficiency and reproducibility of the $^{68}$Ga-chelating agent complex formation. Due to microwave activation, chemical reaction times could be shortened substantially; i.e. the reaction is completed within 2 min or less. This is a clear improvement as a 10 minutes reduction in the reaction time saves about 10% of the $^{68}$Ga radioactivity. Furthermore, microwave activation also leads to fewer side reactions and to an increased radiochemical yield, due to increased selectivity. Suitably, a microwave oven, preferably a monomodal microwave oven is used to carry out microwave activation.

The microwave activation is carried out at 80 to 120 W, preferably at 90 to 110 W, particularly preferably at about 100 W. Suitable microwave activation times range from 20 s to 2 min, preferably from 30 s to 90 s, particularly preferably from 45 s to 60 s. Temperature control of the reaction is advisable when temperature sensitive chelating agents (eg. bifunctional chelating agents comprising peptides or proteins as targeting vectors), are employed in the method. Duration of the microwave activation should be adjusted in such a way, that the temperature of the reaction mixture does not lead to the decomposition of the chelating agent and/or the targeting vector. If chelating agents used in the method according to the invention comprise peptides or proteins, higher temperatures applied for a shorter time are generally more favourable than lower temperatures applied for a longer time period.

The method of the second aspect is preferably either carried out in a sterile manner throughout under aseptic manufacture conditions, or subjected to terminal sterilisation, such that the product is a $^{68}$Ga-labelled radiopharmaceutical composition. Alternatively, the radiopharmaceuticals may also be prepared under non-sterile conditions, followed by terminal sterilisation using e.g. gamma-irradiation, autoclaving, dry heat or chemical treatment (e.g. with ethylene oxide).

In a third aspect, the present invention provides an apparatus suitable for carrying out the method of the second aspect, which comprises:
  (i) a $^{68}$Ga generator;
  (ii) a supply of:
    (a) the aqueous chloride ion solution as defined in the first aspect;
    (b) the chelating agent as defined in the second aspect;
    (c) water or aqueous buffer solution as defined in step (iii) of the first aspect;
  (iii) an anion exchange resin as defined in as defined in the first aspect;
  (iv) a reaction vessel with optional means for heating said vessel;
  (v) a collection container for the $^{68}$Ga-radiolabelled metal complex product;
  (vi) means for transferring the solutions comprising suitable valves and connecting tubing.

The invention is illustrated by Examples 1 and 2. Example 1 provides a method of the invention. Example 2 provides a preparation of a $^{68}$Ga complex using the $^{68}$Ga from Example 1.

Example 1

$^{68}$Ga Elution Using Chloride Ion Solution

A commercial $^{68}$Ga-generator (from Obinsk) having a TiO$_2$ column was eluted with 4M NaCl containing 0.1 M HCl. The same yield of $^{68}$Ga was obtained as when eluting with 0.1 M HCl alone. The $^{68}$Ga eluate obtained was subsequently trapped as GaCl$_4^-$ directly on a strong anion exchange resin with an efficiency of at least 90%.

$^{68}$Ge breakthrough in preliminary experiments was observed to be 2-3 times higher compared to elution with 0.1M HCl alone. This, however, should not have a noticeable effect on the lifetime of the generator, neither would this cause any problems with the radionuclidic purity of the labelled products, since one of the benefits of pre-concentration is the purification from $^{68}$Ge, which also has been shown earlier, and also here in this work preliminary results point in the same direction. This method will purify gallium from most other contaminating cations, except iron, which has very similar complex forming properties to gallium.

Example 2

Preparation of a $^{68}$Ga Metal Complex

The $^{68}$Ga solution from Example 1 was used successfully on a FASTlab automated synthesizer apparatus (GE Healthcare) for the automated production of Neuroendocrine tumor diagnostic radiopharmaceutical (68Ga-DOTATOC).

What is claimed is:
1. A method of obtaining $^{68}$Ga by:
  (i) eluting a $^{68}$Ge/$^{68}$Ga radioisotope generator with a chloride ion solution which comprises 0.05-0.2 M aqueous hydrochloric acid solution and has a total chloride ion solution of 3 to 5 M concentration, wherein said solution has a pH of less than 2, to give an eluate containing $^{68}$Ga as GaCl$_4^-$;
  (ii) passing the eluate from step (i) down an anion exchange resin, wherein the $^{68}$GaCl$_4^-$ is trapped on the resin;
  (iii) eluting the trapped $^{68}$GaCl$_4^-$ from step (ii) with water or aqueous buffer solution, to give an aqueous solution of $^{68}$GaCl$_3$.

2. The method according to claim 1 where the chloride ion solution in step (i) has a chloride ion concentration of 4 molar.

3. The method according to claim 1, where the chloride ion solution is 4M NaCl and further comprises 0.1 M HCl.

4. The method according to claim 1, where the $^{68}$Ge/$^{68}$Ga generator comprises a column comprising titanium dioxide.

5. The method according to claim 1, where water is used in step (iii) to elute $^{68}$Ga from the anion exchanger.

6. The method according to claim 1, where the anion exchange resin comprises quaternary amine functional groups.

7. The method according to claim 1, where the anion exchange resin is based on polystyrene-divinylbenzene.

8. A method of producing a $^{68}$Ga-radiolabelled metal complex which comprises:
  (i) obtaining $^{68}$Ga via the method of claim 1;
  (ii) reacting the $^{68}$Ga from step (i) with a chelating agent, to give the desired $^{68}$Ga metal complex via complexation reaction.

9. The method of claim 8, where the chelating agent is a macrocyclic chelating agent.

10. The method of claim 8, where the chelating agent is a bifunctional chelating agent.

11. The method of claim 10, where the bifunctional chelating agent is conjugated to biological targeting molecule selected from the group consisting of:
  proteins; peptides; carbohydrates, oligonucleotides or organic drug molecules of molecular weight less than 1500 Daltons.

12. The method of claim 8, where the complexation reaction of step (ii) is carried out using microwave activation.

13. The method of claim 8, which is carried out under sterile conditions or subjected to terminal sterilisation such that the product is a $^{68}$Ga-labelled radiopharmaceutical.

14. An apparatus suitable for carrying out the method of claim 8, which comprises:
   (i) a $^{68}$Ga generator;
   (ii) a supply of:
      (a) an aqueous chloride ion solution which comprises 0.05-0.2 M aqueous hydrochloric acid solution and has a total chloride ion solution of 3 to 5 M concentration, wherein said solution has a pH of less than 2;
      (b) the chelating agent;
      (c) water or aqueous buffer solution;
   (iii) an anion exchange resin;
   (iv) a reaction vessel with optional means for heating said vessel;
   (v) a collection container for the $^{68}$Ga-radiolabelled metal complex product;
   (vi) means for transferring the solutions comprising suitable valves and connecting tubing.

* * * * *